US012611539B2

(12) United States Patent
    Raines et al.

(10) Patent No.:    US 12,611,539 B2
(45) Date of Patent:       Apr. 28, 2026

(54) MEDICAL DEVICE LEAD TIP ANCHOR

(71) Applicant: Advanced Neuromodulation Systems, Inc., Plano, TX (US)

(72) Inventors: Aaron Raines, Dallas, TX (US); Chris Crawford, Carrollton, TX (US); Brittany Boudreau, Grapevine, TX (US); Manasi Reardon, Allen, TX (US); Matthew Dion, Dallas, TX (US)

(73) Assignee: Advanced Neuromodulation Systems, Inc., Plano, TX (US)

( * ) Notice:  Subject to any disclaimer, the term of this patent is extended or adjusted under 35 U.S.C. 154(b) by 1263 days.

(21) Appl. No.: 17/473,776

(22) Filed:      Sep. 13, 2021

(65)              Prior Publication Data

US 2023/0102674 A1       Mar. 30, 2023

(51) Int. Cl.
     *A61N 1/05*          (2006.01)
     *A61N 1/375*         (2006.01)

(52) U.S. Cl.
     CPC ......... *A61N 1/0558* (2013.01); *A61N 1/0534* (2013.01); *A61N 1/375* (2013.01)

(58) Field of Classification Search
     CPC .... A61N 1/0558; A61N 1/0534; A61N 1/375; A61N 1/0539; A61N 1/057; A61N 1/059
     See application file for complete search history.

(56)              References Cited

U.S. PATENT DOCUMENTS 8,484,841 B1     7/2013   Burros et al.
     9,844,661 B2    12/2017   Franz et al.
  2014/0350653 A1*  11/2014   Shiroff .................... A61N 1/05
                                                                607/116
  2015/0251004 A1    9/2015   Imran et al.
  2016/0158545 A1*   6/2016   Khairkhahan ......... A61N 1/059
                                                                607/19
  2017/0333704 A1   11/2017   Raines
  2018/0126156 A1*   5/2018   Sparks ................... A61B 5/283
  2020/0061371 A1    2/2020   Raines
  2022/0062624 A1    3/2022   Raines

* cited by examiner

*Primary Examiner* — Ankit D Tejani
*Assistant Examiner* — Joshua Brendon Solomon
(74) *Attorney, Agent, or Firm* — Norton Rose Fulbright US LLP

(57)              ABSTRACT

Systems and methods which provide retractable anchor configurations for medical device leads are described. A retractable anchor may implement a retractable distention composed of a resilient material. The retractable distention may be distended when in a neutral state and may be contracted when in a biased state. A biasing bulkhead may be configured to receive a bias force sufficient to retract the retractable distention. A stylet may be inserted into an axial lumen of a medical device lead having retractable tip anchor structure and may engage the biasing bulkhead to apply a bias force. A stylet knob may be configured to interface with the stylet and provide bias force to be transferred to the biasing bulkhead of the retractable tip anchor structure. Locking the stylet knob on the medical device lead may maintain the bias force applied to the biasing bulkhead until the stylet knob is unlocked.

21 Claims, 4 Drawing Sheets

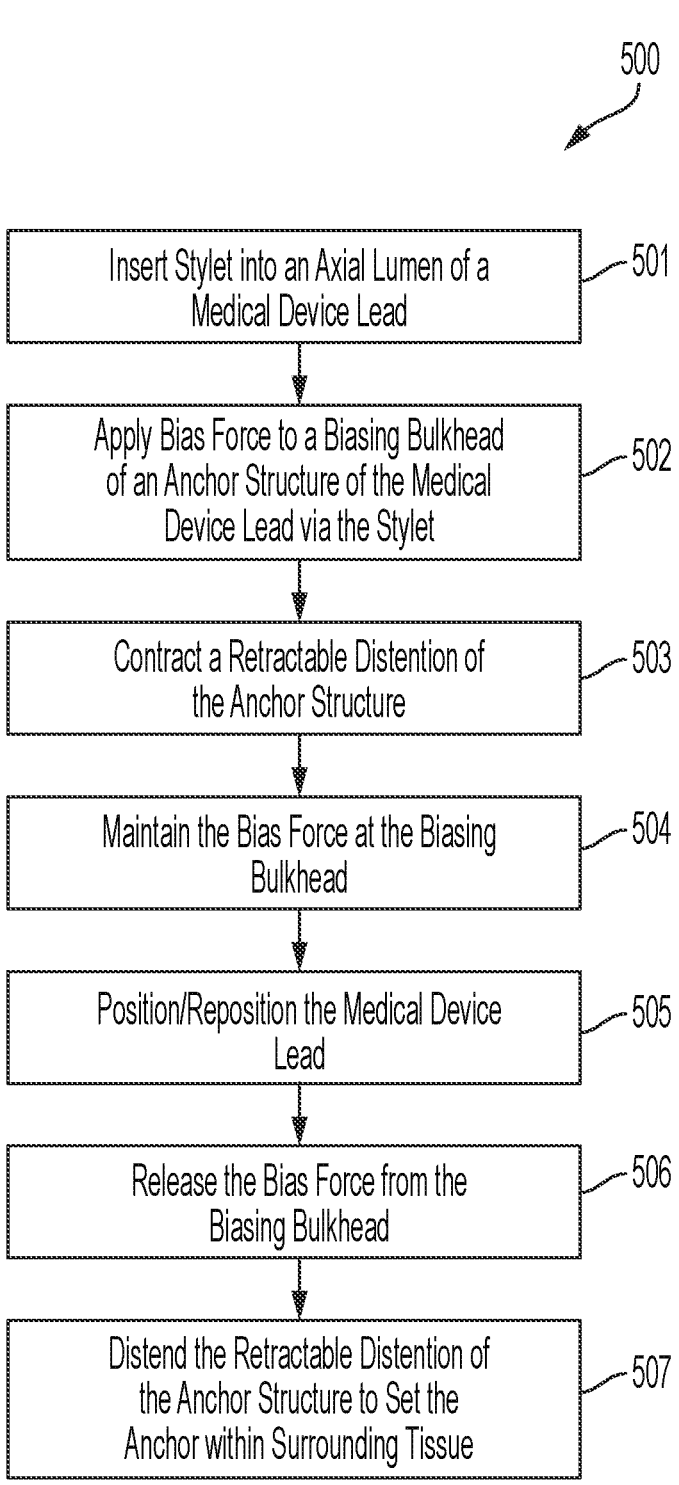

500

Insert Stylet into an Axial Lumen of a Medical Device Lead — 501

Apply Bias Force to a Biasing Bulkhead of an Anchor Structure of the Medical Device Lead via the Stylet — 502

Contract a Retractable Distention of the Anchor Structure — 503

Maintain the Bias Force at the Biasing Bulkhead — 504

Position/Reposition the Medical Device Lead — 505

Release the Bias Force from the Biasing Bulkhead — 506

Distend the Retractable Distention of the Anchor Structure to Set the Anchor within Surrounding Tissue — 507

FIG. 5

MEDICAL DEVICE LEAD TIP ANCHOR

TECHNICAL FIELD

The present invention relates to medical device leads and, more particularly, to retractable tip anchor configurations of implantable medical electrical stimulation leads facilitating small diameter lead implementations and their insertion, anchoring, and removal.

BACKGROUND OF THE INVENTION

Implantable medical devices (IMDs) providing functions such as stimulation of muscle or neurological tissue and/or sensing of physiological occurrences within a human body are used for a wide variety of medical conditions. For example, IMDs in the form of implantable electrical stimulation devices have been commercially distributed that allow electrical pulses or signals to be controllably delivered to targeted tissue or nerves after implantation of the respective device within a patient. Such implantable electrical stimulation devices may be used for cardiac pace making, cardiac rhythm management, treatments for congestive heart failure, implanted defibrillators, and neurostimulation. Neurostimulation encompasses a wide range of applications, such as for example, pain control, nervous tremor mitigation, incontinent treatment, epilepsy seizure reduction, and vagus nerve stimulation for clinical depression. Various neurostimulation techniques have, for example, been shown to be helpful in treating patients with chronic intractable pain.

IMDs in the form of implantable electrical stimulation devices generally include an implanted pulse generator that generates electrical pulses or signals that are transmitted to targeted tissue or nerves through a medical device lead comprising an implantable electrical stimulation lead having electrodes. Medical device leads configured for use with IMDs, such as implantable electrical stimulation devices, typically include connector apparatus (e.g., one or more electrical contacts) disposed on a proximal end and the aforementioned electrodes (e.g., one or more electrically conductive surfaces) disposed on a distal end. Conductive wires (e.g., filars formed from stranded or solid core insulated conductors) interconnect the electrodes at the distal end to corresponding electrical contacts of the connector apparatus at a proximal end. A jacket (e.g., a flexible, resilient member formed biocompatible polymer) is typically included in the body of leads, wherein the conductive wires may be disposed within the jacket and protected from body tissue and other external agents by the jacket. An axial lumen is generally formed within the body of medical device leads (e.g., in the center of a lead body formed from the jacket and extending axially from the proximal end to a point very near a lead tip at the distal end), such as to facilitate manufacture of the lead and/or to accommodate a stylet or similar tool used in implanting the lead.

In use, the medical device lead electrodes are placed within specific areas of the patient's body to provide therapeutic treatment and/or sensing with respect to particular tissue, organs, etc. For example, when used in a stimulation and/or sensing capacity, electrodes of medical device leads are commonly implanted within, near, adjacent, or along various tissue for providing neurostimulation therapy and/or sensing one or more aspects of the surrounding environment. Peripheral nerve stimulation (PNS) techniques, for example, dispose electrodes along peripheral nerves. As another particular example, spinal cord stimulation (SCS) techniques dispose electrodes within the epidural or intrathecal space of the spinal column. In a further example, deep brain stimulation (DBS) disposes electrodes within a specific area of the brain. Other techniques dispose electrodes of a medical device lead in and around other organs or tissue of a patient, such as around the heart.

For those patients who prove unresponsive to conservative pain management techniques, for example, PNS may be a successful therapy for pain management when the pain is known to result from a specific nerve. PNS is based in part on the Melzack-Wall gate control theory of pain. Sweet and Wespic first used electrical stimulation of peripheral nerves in the 1960s to mask the sensation of pain with a tingling sensation (paresthesia) caused by the electrical stimulation. PNS typically involves a procedure in which one or more electrodes of a medical device lead are placed adjacent to a select one of the peripheral nerves. Peripheral nerves are the nerves that are located beyond the brain or spinal cord. Once implanted, the lead may be disposed to extend from the stimulation/sensing site to the location of an associated IMD (e.g., a stimulation generator or a pulse generator). The distance from the stimulation/sensing site to the IMD may, for example, be on the order of 20-100 cm. In some situations, a lead extension may be utilized between a lead and IMD in order to span relatively long distances. In operation, the one or more electrodes deliver electrical pulses as may be generated and provided by the IMD.

It should be appreciated from the foregoing that the electrodes of a medical device lead are generally precisely placed within the patient's body to achieve therapeutic efficacy and/or reduced side effects. Implantation of a medical device lead may, for example, include making an incision near a target area (e.g., stimulation/sensing site), inserting a needle (e.g., 14 gauge to 16 gauge needle) into the target area, and inserting the lead down the needle to the precise site that is to be stimulated. A stylet may be used within an axial lumen of the lead to aid in guiding the insertion of the distal end of the lead into the tissue of the target area and to precisely place the electrodes.

Whether in a stimulation, sensing, and/or element delivery capacity, medical device leads are implanted such that the distal end of the lead having one or more electrodes thereon is adjusted precisely within the an area of placement so as to maintain an orientation, position, spacing, etc. with respect to surrounding tissue to facilitate effective treatment of one or more indications. Current medical device lead designs, however, are often prone to movement (e.g., axially, radially and/or longitudinally) after insertion if steps are not taken to control such movement. Typically, some mechanism is employed to anchor the medical device leads so that the therapeutic agent (e.g., electrical signal) will continue to be delivered to the appropriate site. Accordingly, various forms of anchoring structures have been utilized to discourage movement of the medical device lead and/or the electrodes, such as to facilitate satisfactorily long functional survival time of the lead, to avoid the reprogramming or replacement of the lead to restore effective therapy, etc.

A prior anchor structure for use with implantable medical device leads either slid over the lead or clamped over the lead at a position along the elongated body of the lead on the side proximal to the IMD from the electrodes (i.e., the anchor is disposed near the electrodes on the lead body between the electrodes and the IMD). In some examples, the anchor structure is secured to the medical device lead at the same time the anchor is sutured to the fascia. For example, an anchor may be slid onto the proximal end of a lead body while maintaining the position of the medical device lead within the body of the patient. The anchor may be secured to the medical device lead on the proximal end side of the electrodes by tying ligatures around grooves in the anchor when the anchor is sutured to the fascia or other tissue (e.g., supraspinous ligament). Such existing anchoring solutions can be problematic. For example, an appreciable length of the distal end of the lead upon which the electrodes are disposed extends beyond the anchor. Accordingly, although the anchor may prevent or reduce movement of a portion of the lead near the electrodes more proximal to the IMD, appreciable movement or displacement of the distal end of the lead including the electrodes may be experienced. Moreover, this anchor structure can necessitate an invasive procedure, such as to cut ligatures, sutures, etc., for removal or repositioning of the medical device lead.

In another example of a prior anchor structure for use with implantable medical device leads, one or more tines of a tine anchor are disposed at a position along the elongated body of the lead more proximal to the IMD than are the electrodes. In some examples, a plurality of tines are distributed radially about the circumference of a medical device lead on the proximal end side of the electrodes. The tines are sufficiently flexible to allow the plurality of tines to hinge with respect to the elongated body of the lead to thereby provide barb structures to engage with surrounding tissue. Tines of this anchor structure are sufficiently rigid to allow the plurality of tines to hold a shape and angle in order to discourage displacement or movement of the medical device lead. The tines are disposed on the proximal side of the electrodes to allow the electrodes to be exposed for intra-operative testing (e.g., delivery of stimulation through the electrodes to the tissue, with the patient reporting whether stimulation is felt in the intended location) while keeping the tines undeployed in the needle or introducer (e.g., if the tines were disposed on the distal end beyond the electrodes, the tines would have to deploy before correct lead location is confirmed via intra-operative testing). These existing anchoring solutions can also be problematic. For example, as with the previously described anchor structure, an appreciable length of the distal end of the lead upon which the electrodes are disposed extends beyond the anchor. Accordingly, appreciable movement or displacement of the distal end of the lead including the electrodes may be experienced. Moreover, the tines of this anchor structure can result in damage to surrounding tissue in situations where the medical device lead is removed or repositioned. For example, the tines of existing anchor solutions are generally not retractable, and thus repositioning or removal of the medical device lead involves overwhelming the holding forces of the plurality of tines deployed in the tissue surrounding the lead or invasive blunt tissue dissection to expose and then loosen the tines from surrounding tissue.

The size of current medical device leads used as implantable stimulation leads for various neuromodulation stimulation techniques can present challenges with respect to providing anchor structures configured to address the above-mentioned problems. For example, implantation techniques such as PNS, and even SCS, using needles to insert the lead to the precise site that is to be stimulated can demand very small diameter (e.g., 1 mm to 1.4 mm outer diameter) lead bodies and electrodes. Implementing anchor structures well suited for discouraging movement or displacement of a portion of the lead comprising the electrodes which is configured for insertion, anchoring, and removal has proved challenging, particularly with respect to small diameter lead bodies.

BRIEF SUMMARY OF THE INVENTION

The present invention is directed to systems and methods which provide retractable tip anchor configurations for medical device leads facilitating small diameter lead implementations and/or which facilitate insertion, anchoring, and removal of the lead. Retractable tip anchors of embodiments of the invention may, for example be utilized with respect to various configurations of implantable electrical stimulation leads. Embodiments of retractable tip anchors implemented according to concepts herein may provide a small diameter (e.g., 1 mm to 1.4 mm outer diameter) when retracted enabling and facilitating medical device leads implementing the anchor structure being configured for insertion into a target area via needle (e.g., 14 gauge to 16 gauge needle). Medical device leads comprising one or more retractable tip anchor of some embodiments of the present invention may thus be well suited for use in peripheral nerve stimulation (PNS) techniques and/or spinal cord stimulation (SCS) techniques.

A retractable tip anchor of embodiments of the invention may implement a retractable distention composed of a resilient polymeric material. According to embodiments, the retractable distention may be distended when in a neutral state and may be contracted when in a biased state. In use according to some examples, the retractable distention may transition to a biased state and being contracted when a bias force is applied, and may transition to a neutral state and being distended when the bias force is removed.

Retractable tip anchor structures implementing a retractable tip anchor configuration of embodiments of the invention may, for example, include a retractable distention formed in an elongated body of a medical device lead having an axial lumen and a biasing bulkhead terminating the axial lumen. The retractable distention of some examples may be composed of a resilient polymeric material formed as a surface perturbation in the elongated body which is distended when in a neutral state and is contracted when in a biased state. The biasing bulkhead of some examples may be configured to receive a bias force sufficient to retract the retractable distention. In accordance with embodiments of the invention, the retractable tip anchor structure is disposed on the medical device lead distally with respect to electrodes of the lead (e.g., the retractable tip anchor is disposed more near the distal end termination point of the medical device lead than are electrodes disposed along the distal end of the medical device lead). In operation according to embodiments of the invention, deployment of a retractable tip anchor provides anchoring of a medical device lead without affecting or moving the placement of the lead electrodes.

In operation according to embodiments, a stylet may be inserted into an axial lumen of a medical device lead having retractable tip anchor structure disposed upon a distal end portion of the lead. A distal end of the stylet may engage a biasing bulkhead of the retractable tip anchor structure and apply a bias force thereto. Sufficient bias force may be applied according to examples so as to contract the retractable distention. Thereafter, the distal end of the medical device lead may be positioned and/or repositioned. For example, the distal end of a medical device lead having a retractable distention of retractable tip anchor structure thereon may be implanted (e.g., inserted via a needle) into tissue of a patient. Once positioned as desired, the stylet may be retracted and the bias force removed so as to allow the retractable distention to return to a neutral state in which the retractable distention is distended. The foregoing functions may be repeated so that the retractable tip anchor may be deployed and retracted if repositioning of the medical device lead is desired.

The lead body surface perturbation of the retractable distention of embodiments herein may be contracted to a point that the retractable distention becomes substantially of uniform diameter with the lead body. Accordingly, retractable tip anchor structures implemented in accordance with concepts herein are well suited for use in situations where a medical device lead is of a small diameter (e.g., 1 mm to 1.4 mm outer diameter of PNS and SCS examples). In particular, retractable tip anchor structures of embodiments facilitate use of relatively non-invasive implantation techniques (e.g., implantation via needle) and explantation techniques (e.g., removal of the lead without cutting tissue, ligatures, or sutures, without further damaging surrounding tissue, such as by overwhelming the holding force of a tine, etc.).

Retractable tip anchor structures implementing a retractable tip anchor configuration of some embodiments may include a stylet knob configured to interface with a proximal end of the stylet and provide bias force to be transferred via the stylet to the biasing bulkhead of the retractable tip anchor structure. The retractable distention of the retractable tip anchor structure may, for example, be contracted by fully inserting the stylet into an axial lumen of a medical device lead having the retractable tip anchor structure disposed at a distal end thereof and introducing bias force to the stylet knob. For example, the stylet knob may be pushed or otherwise moved towards the distal end of the medical device lead along a direction of the axial lumen to transfer the bias force to the biasing bulkhead via the stylet. According to some embodiments, the stylet knob may be configured to lock on to a proximal end of the medical device lead. Locking the stylet knob on the proximal end of the medical device lead may maintain the bias force applied to the biasing bulkhead until the stylet knob is unlocked.

In operation according to embodiments, a retractable tip anchor may be deployed (e.g., the anchor "set" within surrounding tissue) by unlocking the stylet knob from the proximal end of a medical device lead and backing stylet out. This operation allows the distal end of the medical device lead to be steered into position while the retractable distention is contracted and then further movement of the distal end of the medical device lead to be discouraged when the retractable distention is distended after the stylet knob is unlocked. The distended retractable distention of embodiments engages or otherwise interacts with the tissue surrounding the distal end of the medical device lead and discourages movement of the distal end of the medical device lead, thus locking the distal end of the lead into position.

It should be appreciated that retractable tip anchor of embodiments of the invention solves problems with respect to a portion of the distal end of a medical device lead extending distally beyond the lead electrodes being prone to movement (e.g., when traditional anchors are used). For example, retractable tip anchor structure integrated into the distal tip (e.g., more toward the distal end of the lead than the electrodes) of a medical device lead may minimize or mitigate migration of the distal end of the lead from body motion. Moreover, retractable tip anchor of embodiments facilitate removal and/or repositioning of the medical device lead without employing an invasive procedure and without further damage to surrounding tissue. For example, the retractable distention of a retractable tip anchor may be contracted, after the anchor having initially been set, by reinserting the stylet into the medical device lead and providing a suitable bias force.

The foregoing has outlined rather broadly the features and technical advantages of the present disclosure in order that the detailed description that follows may be better understood. Additional features and advantages will be described hereinafter which form the subject of the claims herein. It should be appreciated by those skilled in the art that the conception and specific embodiments disclosed may be readily utilized as a basis for modifying or designing other structures for carrying out the same purposes of the present designs. It should also be realized by those skilled in the art that such equivalent constructions do not depart from the spirit and scope as set forth in the appended claims. The novel features which are believed to be characteristic of the designs disclosed herein, both as to the organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present disclosure.

BRIEF DESCRIPTION OF THE DRAWINGS

FIG. 5 shows a block diagram of a flow providing operation to anchor a medical device lead using retractable anchor structure according to embodiments of the present invention.

DETAILED DESCRIPTION OF THE INVENTION

Retractable tip anchor configurations are provided according to embodiments of the invention for use in anchoring or otherwise discouraging movement of medical device leads. For example, retractable tip anchor structures of embodiments may be utilized with respect to medical device leads in the form of implantable medical electrical stimulation leads comprising part of an implantable medical device operable to deliver electrical pulses or signals to a targeted tissue or nerves. Medical device leads comprising a retractable tip anchor of some embodiments of the present invention may, for example, be configured for use in peripheral nerve stimulation (PNS) techniques and/or spinal cord stimulation (SCS) techniques.

To aid in understanding concepts herein, the description that follows describes examples relating to implantable medical devices of a PNS system. However, it is to be understood that, while embodiments of a retractable tip anchor are well suited for applications in PNS, the disclosure in its broadest aspects may not be so limited. Rather, the disclosure may be used with any type of implantable therapy delivery system with one or more therapy delivery elements. For example, the present disclosure may be used as part of a pacemaker, a defibrillator, a cochlear stimulator, a retinal stimulator, a stimulator configured to produce coordinated limb movement, a cortical stimulator, a deep brain stimulator, spinal column stimulator, microstimulator, or in any other neural stimulator configured to treat various indications.

A retractable tip anchor according to concepts herein may be utilized with one or more therapy delivery elements comprising an electrical lead including one or more electrodes to deliver pulses or signals to a respective target tissue site in a patient. Additionally or alternatively, a retractable tip anchor may be utilized with one or more therapy delivery elements comprising an electrical lead including sensing electrodes to sense physiological parameters (e.g., blood pressure, temperature, cardiac activity) at a target tissue site within a patient.

In the various embodiments contemplated by this disclosure, therapy may include stimulation therapy, sensing or monitoring of one or more physiological parameters, fluid delivery, and the like. A therapy delivery element (also referred to as a medical device lead or simply a lead) may include pacing or defibrillation leads, stimulation leads, sensing leads, extensions for any of the above, or combinations thereof. A target tissue site may refer generally to the target site for implantation of a therapy delivery element, regardless of the type of therapy.

Figure 1A:
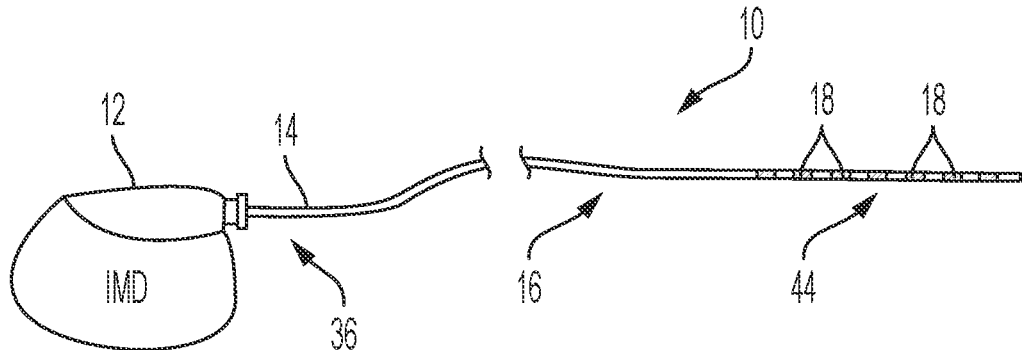
FIGS. 1A and 1B illustrate example stimulation systems as may utilize embodiments of retractable tip anchor configurations of embodiments of the present invention.
Figure 1B:
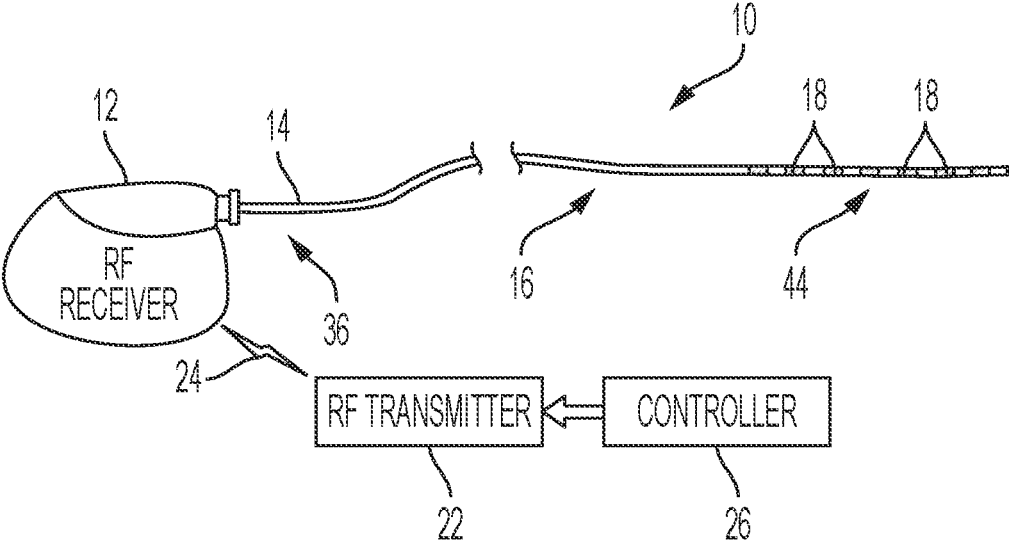

FIGS. 1A and 1B illustrate example neurological stimulation systems 10 for electrically stimulating a predetermined site, for example, a peripheral nerve, to provide therapeutic treatment and/or sensing (e.g., to treat one or more indications). In general terms, stimulation system 10 includes implantable medical device (IMD) 12 (e.g., an IMD in the form of an implantable electrical stimulation device) and one or more implantable medical device leads comprising implantable electrical stimulation leads having electrodes. IMD 12 provides a stimulation source (e.g., a pulse generator that generates electrical pulses or signals for transmission to targeted tissue or nerves). Accordingly, the illustrated example of stimulation system 10 includes electrical stimulation lead 14 for applying electrical stimulation pulses to a predetermined site. Although only one electrical stimulation lead 14 is shown, often two or more leads are used with the therapy delivery system 10.

Electrical stimulation lead 14 includes elongated body 16, such as may be composed of a suitable electrically insulative material (e.g., a polymer, such as polyurethane or silicone), having proximal end 36 and distal end 44. Elongated body 16 of electrical stimulation lead 14 of some embodiments may, for example, have a diameter of between about 1 mm to 1.8 mm and a length within the range of 30 cm to 90 cm. In the illustrated embodiment, proximal end 36 of electrical stimulation lead 14 is electrically coupled to IMD 12, such as via a connector assembly (not visible in the figures). As shown in the illustrated example, electrical stimulation lead 14 may include one or more neurostimulation electrodes 18 located on distal end 44 of elongated body 16 of the lead.

IMD 12 of embodiments may include an electronic subassembly having control and pulse generation circuitry (e.g., implantable pulse generator, not shown) for delivering electrical stimulation energy to neurostimulation electrodes 18 of electrical stimulation lead 14 in a controlled manner. IMD 12 of some examples may thus include a power supply, such as a battery. The housing of IMD 12 may be composed of a biocompatible material, such as for example titanium, forming a hermetically sealed compartment containing the electronic subassembly and power supply and providing protection from the body tissue and fluids. A connector assembly may be disposed in a portion of the housing that is, at least initially, not sealed and is configured to receive proximal end 36 of electrical stimulation lead 14 having electrical contacts configured to electrically couple the lead to an implantable pulse generator of IMD 12. The connector assembly may, for example, comprise a plurality of contacts that electrically couple with respective terminals at proximal end 36 of electrical stimulation lead 14 (or an optional extension lead, if present). Electrical conductors extend from the connector assembly and connect to the electronic subassembly of IMD 12 of examples.

In operation of stimulation system 10, IMD 12 provides a programmable stimulation signal (e.g., in the form of electrical pulses or substantially continuous-time signals) that is delivered to target stimulation sites by neurostimulation electrodes 18. Accordingly, one or both of IMD 12 and electrical stimulation lead 14 are implanted in or on a subject's body. In certain embodiments, IMD 12 is coupled to electrical stimulation lead 14, such as through one or more electrical contacts of a connector apparatus disposed on proximal end 36 of the lead. IMD 12 of some examples may be coupled to electrical stimulation lead 14 via an optional implantable extension lead (not shown). In certain other embodiments, IMD 12 is incorporated into electrical stimulation lead 14 (e.g., IMD 12 may be integrated with or embedded within electrical stimulation lead 14).

Whether IMD 12 is coupled to or incorporated into electrical stimulation lead 14, IMD 12 controls the stimulation pulses transmitted to one or more neurostimulation electrodes 18 located on distal end 44 of the lead, positioned in communication with a predetermined target area (e.g., stimulation/sensing site), according to suitable stimulation parameters (e.g., duration, amplitude or intensity, frequency, pulse width, etc.). In applications with more than one electrical stimulation lead 14, implantable pulse generator 12 may provide the same or a different signal to neurostimulation electrodes 18 for providing stimulation signals delivered to the predetermined target area.

The predetermined target area in communication with electrical stimulation lead 14 is a peripheral nerve according to some examples. Peripheral nerves can include cranial nerves for example, olfactory nerve, optic nerve, oculomotor nerve, trochlear nerve, trigeminal nerve, abducens nerve, facial nerve, vestibulocochlear (auditory) nerve, glossopharyngeal nerve, vagal nerve, accessory nerve, and the hypoglossal nerve. In addition to cranial nerves, the predetermined target area can be a dermatome area, for example, C2, C3, C4, C5, C6, C7, C8, as well as any thoracic, lumbar or sacral dermatome. Other dermatomes that can be included as target areas according to embodiments of the present invention include dermatomes associated with cranial nerves having somatosensory function, for example, but not limited to dermatomes associated with the trigeminal nerve, intermediate part of the facial nerve, glossopharyngeal nerve, or vagal nerve. Peripheral nerves also includes spinal nerves, which in general, are named after the vertebral segment of the spinal column above their origin. For example, the spinal nerve originating under the third thoracic vertebra may be termed the third thoracic nerve. Thus, spinal nerves can include, but are limited to cervical nerve roots (e.g., C1, C2, C3, C4, C5, C6, C7 and C8), thoracic nerve roots (e.g., T1, T2, T3, T4, T5, T6, T7, T8, T9, T10, T11, T12), lumbar nerve roots (L1, L2, L3, L4, L5) sacral nerve roots (e.g., S1, S2, S3, S4, S5) and the coccygeal nerve. Other peripheral nerves are spinal nerves such as the suboccipital nerve, the greater occipital nerve, the lesser occipital nerve, the greater auricular nerve, the lesser auricular nerve, the phrenic nerve, and the brachial plexus, which branches to form the dorsal scapular nerve, the thoracic nerve, the suprascapular nerve, the lateral pectoral, the musculocutaneous nerve, the axillarily nerve, the radial nerve, the median nerve, the ulnar nerve, the intercostal nerves, and other minor peripheral nerves, as well as parasympathetic and/or sympathetic nerves. In certain embodiments, the peripheral nerve stimulated is the trigeminal nerve or the trigeminal dermatome or any peripheral nerve associated with the C2 dermatome area, C3 dermatome area, cranial nerves, the median nerve or any combination thereof. Peripheral nerve ganglia, which are collections of peripheral nerve cell bodies, may be predetermined target areas in communication with electrical stimulation lead 14 in certain embodiments.

In certain embodiments, transcutaneous implantation of electrical stimulation lead 14 is used either permanently or temporarily. Neurostimulation electrodes 18 of electrical stimulation lead 14 may, for example, be precisely placed in communication with a target area within the patient's body through a implantation technique in which an incision is made near the target area, a needle (e.g., 14 gauge to 16 gauge needle) is inserted into the target area, and distal end 44 of electrical stimulation lead 14 comprising neurostimulation electrodes 18 is inserted down the needle to the precise site that is to be stimulated. A stylet may be used within an axial lumen of electrical stimulation lead 14 to aid in guiding the insertion of the distal end of the lead into the tissue of the target area and to precisely place the electrodes.

IMD 12 may, for example, be implanted in a surgically-made pocket, such as in the abdomen or above the buttocks. IMD 12 may, of course, also be implanted in other locations of the patient's body. Use of an extension lead facilitates locating IMID 12 away from an exit point of electrical stimulation lead 14. Additionally or alternatively, and extension lead may serve as a lead adapter if proximal end 36 of electrical stimulation lead 14 is not compatible with the connector assembly of IMD 12, since different manufacturers use different connectors at the ends of their stimulation leads and are not always compatible with a connector assembly of a particular IMD.

Since IMD 12 of embodiments is located remotely from the target area for therapy, electrical stimulation lead 14 (and one or more extension leads, when present) may be routed through subcutaneously formed pathways (e.g., along the torso of the patient) to a subcutaneous pocket where IMD 12 is located.

Electrical stimulation lead 14 of embodiments may be fixed in place near the target area selected by the clinician using one or more anchors. For example, an anchor may be positioned on electrical stimulation lead 14 in a wide variety of locations and orientations along elongated body 16 to accommodate individual anatomical differences and the preferences of the clinician. In a typical implementation, an anchor may be disposed on distal end 44 of elongated body 16 on the side of neurostimulation electrodes 18 towards proximal end 36 (e.g., disposed on the distal end more near to the IMD than are the electrodes). Such an anchor may then be affixed to tissue using fasteners, such as for example, one or more sutures, staples, screws, or other fixation devices. The tissue to which an anchor is affixed may include subcutaneous fascia layer, bone, or some other type of tissue. Securing the anchor to tissue in this manner reduces the chance that electrical stimulation lead 14 will become dislodged or will migrate in an undesired manner.

A doctor, the patient, or another user of IMD 12 may directly or indirectly input stimulation parameters to specify or modify the nature of the stimulation provided. Some embodiments may, for example, employ a burst stimulus. In an example, burst stimulus comprises a frequency in the range of about 1 Hz to about 300 Hz, more particular, in the range of about 1 Hz to about 12 Hz, and more particularly, in the range of about 1 Hz to about 4 Hz, 4 Hz to about 7 Hz or about 8 Hz to about 12 Hz, 18 Hz to 20 Hz, and 40

Hz. The burst stimulus comprises at least two spikes, for example, each burst stimulus can comprise about 12 to about 100 spikes, more particularly, about 2 to about 10 spikes. Each spike can comprise a frequency in the range of about 50 Hz to about 1000 Hz, more particularly, in the range of about 200 Hz to about 500 Hz. The interval between spikes can be about 0.5 milliseconds to about 100 milliseconds. The frequency of the spikes within the burst does not need to be constant or regular, in fact, typically, the frequency of the spikes is random or variable. In further embodiments, the burst stimulus is followed by an inter-burst interval. The inter-burst interval has a duration in the range of about 5 milliseconds to about 5 seconds, more preferably, about 10 milliseconds to about 300 milliseconds, or any range therebetween. It is envisioned that the burst stimulus has a duration in the range of about 10 milliseconds to about 5 seconds, more particularly in the range of about 250 milliseconds to 1 second. The burst stimulus and the inter-burst interval can have a regular pattern or an irregular pattern (e.g., random or irregular harmonics).

In accordance with some embodiments, IMD 12 can take the form of an implantable receiver-stimulator in which the power source for powering the implanted receiver and/or control circuitry to command the receiver-stimulator are provided externally. Control circuitry and a power source of some examples may be contained in an external controller which is inductively coupled to a receiver-stimulator configuration of IMD 12 via an electromagnetic link. IMD 12 in the embodiment shown in FIG. 1B, for example, includes an implantable wireless receiver. The wireless receiver of this example is capable of receiving wireless signals from wireless transmitter 22 operable under control of controller 26, both of which are located external to the person's body. In some embodiments, the wireless transmitter may be stand-alone and no external controller 26 is required. The wireless signals are represented in FIG. 1B by wireless link symbol 24. A doctor, the patient, or another user of IMD 12 may use controller 26 to provide control signals for operation of IMD 12. Controller 26 may, for example, provide the control signals to wireless transmitter 22, wireless transmitter 22 transmits the control signals and power to wireless receiver of IMD 12, and IMD 12 uses the control signals to vary the stimulation parameters of stimulation pulses transmitted through electrical stimulation lead 14 to the target area (e.g., predetermined peripheral nerve). Thus, external controller 26 can be for example, a handheld programmer, to provide a means for programming the IMD.

In still other embodiments, IMD 12 can take the form of an external trial stimulator (ETS), which has similar pulse generation circuitry as an implantable pulse generator (IPG), but differs in that it is a non-implantable device that is used on a trial basis after electrical stimulation lead 14 has been implanted and prior to implantation of an IPG, to test the responsiveness of the stimulation that is to be provided.

Medical device leads, such as electrical stimulation lead 14, are typically fixed in place near the location selected by the clinician using one or more anchors. Accordingly, irrespective of the particular configuration of IMD 12, electrical stimulation lead 14 of embodiments may utilize a retractable tip anchor configuration of the present invention. For example, electrical stimulation lead 14 shown in FIGS. 1A and 1B may comprise embodiments of retractable tip anchors implemented according to concepts herein.

Figure 2A:
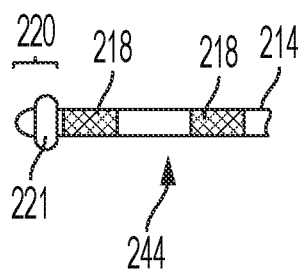
FIGS. 2A and 2B show an example of retractable tip anchor structure provided with respect to a medical device lead according to embodiments of the present invention.
Figure 2B:
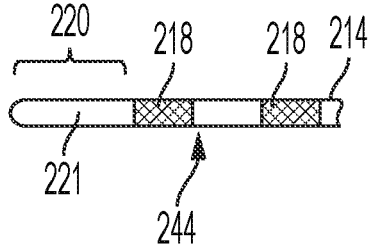

FIGS. 2A and 2B show an example embodiment of retractable tip anchor structure 220 of a retractable tip anchor configuration provided with respect to medical device lead 214 in accordance with concepts of the present invention. According to some examples, medical device lead 214 may correspond to embodiments of electrical stimulation lead 14, while electrodes 218 may correspond to electrodes 18, of FIGS. 1A and 1B. It should be appreciated that, in addition to distal end 244 portion shown in FIGS. 2A and 2B, medical device lead 214 includes a proximal end (not shown), such as may correspond to proximal end 36 of FIGS. 1A and 1B. Further, medical device lead 214 of examples herein may include electrical contacts disposed on the proximal end which are in electric communication with corresponding ones of electrodes 218.

As shown in FIGS. 2A and 2B, retractable tip anchor structure 220 embodiments is disposed on distal end 244 portion of medical device lead 214. The illustrated example provides retractable tip anchor structure 220 disposed on medical device lead 214 distally with respect to electrodes 218. That is, a retractable tip anchor of retractable tip anchor structure 220 of this example is disposed more near the distal end termination point of medical device lead 214 than are electrodes 218 disposed along distal end 244 portion of medical device lead 214.

Retractable tip anchor structure 220 of the illustrated example includes an elongated body portion. As shown in FIG. 2A, retractable tip anchor structure 220 implements a retractable tip anchor configuration which includes retractable distention 221 disposed at a position along the elongated body. The elongated body portion and/or retractable distention 221 may be composed of a resilient polymeric material (e.g., polyurethane or silicone). For example, the elongated body portion of retractable tip anchor structure 220 may be formed to provide a substantially uniform diameter with the lead body of medical device lead 214 having retractable distention 221 disposed thereon. Retractable distention 221 may be formed as a surface perturbation in the elongated body of medical device lead 214.

FIG. 2A shows retractable distention 221 in a neutral state in which retractable distention 221 is distended (e.g., the surface perturbation of retractable distention 221 is pronounced and is of non-uniform diameter with the lead body of medical device lead 214). In contrast, FIG. 2B shows retractable distention 221 in a biased state in which retractable distention 221 is contracted (e.g., the surface perturbation of retractable distention 221 is diminished and is substantially of uniform diameter with the lead body of medical device lead 214). Retractable distention 221 of embodiments transitions to the biased state and being contracted (e.g., FIG. 2B) when a bias force is applied with respect to retractable tip anchor structure 220, and transitions to the neutral state and being distended (e.g., FIG. 2A) when the bias force is removed with respect to retractable tip anchor structure 220.

Figure 3A:
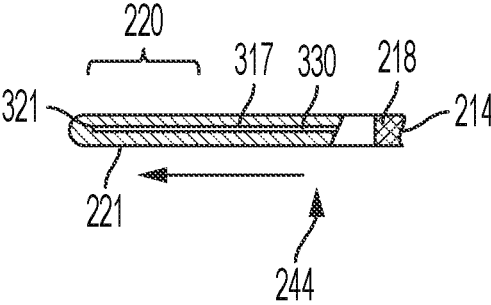
FIGS. 3A and 3B show partial cutaway views of the retractable tip anchor structure and medical device lead of FIGS. 2A and 2B.
Figure 3B:
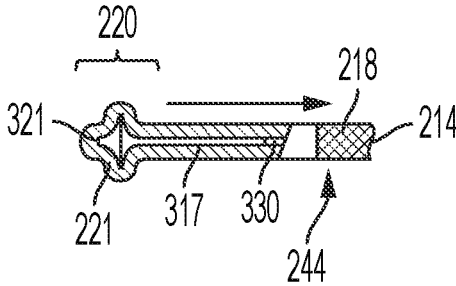

As shown in the partial cutaway views of FIGS. 3A and 3B, medical device lead 214 may include axial lumen 317 provided within the elongated body of the lead. Axial lumen 317 may, for example, provide an orifice at a proximal end of the elongated body of medical device lead 214 and extend to a termination point within distal end 244 of the elongated body medical device lead 214. It can be seen in the illustrated example, that the distal end of axial lumen 317 passes through retractable tip anchor structure 220 such that the elongated body portion of the retractable tip anchor structure includes an axial lumen.

Axial lumen 317 of embodiments may accept insertion of stylet 330 (e.g., a relatively stiff member, such as a slender metal probe), such as for use in stiffening and/or shaping medical device lead 214 for implantation. As described above, axial lumen 317 of the illustrated embodiment extends through the elongated body portion of retractable tip anchor structure 220. Accordingly, stylet 330 may additionally or alternatively be utilized according to embodiments of the invention for retracting and deploying the retractable tip anchor (e.g., control contracting and distending retractable distention 221), as described in further detail below.

Retractable tip anchor structure 220 of the illustrated embodiment biasing bulkhead 321 terminating the axial lumen within the elongated body portion of the retractable tip anchor structure. Biasing bulkhead 321 of embodiments is configured to receive a bias force sufficient to retract retractable distention 221. For example, biasing bulkhead 321 may comprise a rigid member, such as a ball or cylinder of hard plastic, disposed at the terminal end of axial lumen 317. Additionally or alternatively, biasing bulkhead 321 may comprise a reinforced (e.g., thickened, hardened, etc.) tip portion of the elongated body portion of retractable tip anchor structure 220.

In accordance with embodiments of the invention, biasing bulkhead 321 is configured to interface with a distal end of stylet 330 and receive a bias force applied via the stylet. For example, biasing bulkhead 321 is configured to receive a bias force applied in an axial direction corresponding to the axial lumen, such as by operation to press or push stylet 330 toward biasing bulkhead 321 while disposed within axial lumen 317. For example, as shown in FIG. 3A, stylet 330 may be inserted into axial lumen 317, interfaced with biasing bulkhead 321, and a bias force applied to a proximal end of stylet 330 transferred to retractable tip anchor structure 220 via biasing bulkhead 321, whereby retractable distention 221 transitions to the biased state and being contracted. Correspondingly, as shown in FIG. 3B, stylet 330 may be moved (e.g., extracted or partially extracted from) within axial lumen 317 so as to disengage biasing bulkhead 321, or otherwise release the bias force on the biasing bulkhead, whereby retractable distention 221 transitions to the neutral state and being distended.

Retractable tip anchor structures implementing a retractable tip anchor configuration of some embodiments of the invention may include a stylet knob configured to interface with a proximal end of the stylet and provide the bias force to be transferred via the stylet to the biasing bulkhead of the retractable tip anchor structure. Accordingly, in addition to retractable distention 221 and biasing bulkhead 321, retractable tip anchor structure 220 may include a stylet knob, such as stylet knob 420 shown in FIGS. 4A and 4B. In operation according to embodiments of the invention, stylet 330 may be fully inserted into axial lumen 330 so that a distal end thereof interfaces with biasing bulkhead 321. Thereafter, stylet knob 420 of embodiments may be positioned on the proximal end of medical device lead 214 to interface with stylet 330 and subsequently pushed or otherwise moved towards the distal end of medical device lead 214, along a direction of axial lumen 317, to introduce and transfer a bias force to biasing bulkhead 321 via stylet 330.

Figure 4A:
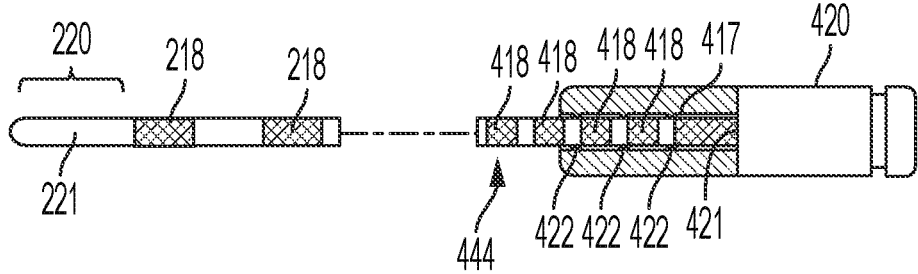
FIGS. 4A and 4B show an example of a stylet knob according to embodiments of the present invention.
Figure 4B:
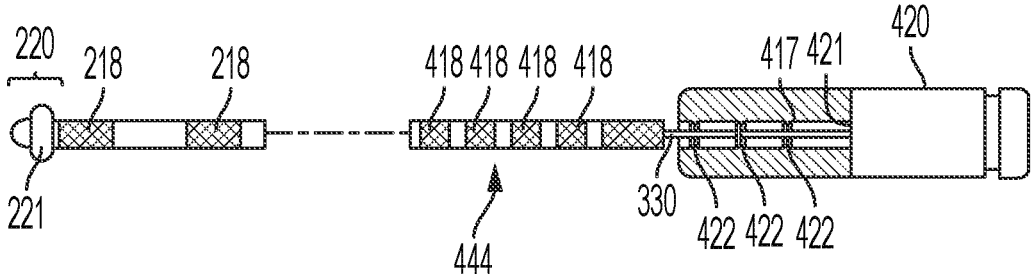

As shown in the partial cutaway views of FIGS. 4A and 4B, stylet knob 420 of the illustrated example includes interface lumen 417 configured to receive a portion of the elongated body at proximal end 444 of medical device lead 214. For example, interface lumen 417 may be sized and shaped to closely conform to a size and shape of the outer surface of the elongated body at proximal end 444 of medical device lead 214. In accordance with embodiments of the invention, terminal end 421 (e.g., shown at the edge of the partial cutaway in FIGS. 4A and 4B) of interface lumen 417 is configured to interface with a proximal end of stylet 330 and apply a bias force sufficient to retract retractable distention 221 thereto. For example, stylet knob 420 may be formed of a rigid polymer (e.g., hard plastic, hard urethane, etc.) such that terminal end 421 of interface lumen 417 is of sufficient rigidity for transferring a bias force to stylet 330. Additionally or alternatively, terminal end 421 may be provided with a rigid member, such as a ball or cylinder of hard plastic, for interfacing with the proximal end of stylet 330 and transferring a bias force thereto.

Stylet knob 420 of embodiments is configured to lock onto a proximal end of medical device lead 214 and maintain application of a bias force at biasing bulkhead 321 via stylet 330. Interface lumen 417 may, for example, be configured to provide an interference fit with proximal end 444 of medical device lead 214 (e.g., the inner diameter of interference lumen 417 may be slightly smaller than the outer diameter of the elongated body of medical device lead 214 at proximal end 444). In accordance with interference fitment of examples, friction between surfaces of stylet knob 420 and medical device lead 214 may lock stylet knob 420 onto medical device lead 214 sufficiently to maintain a bias force applied by stylet 330 at biasing bulkhead 321. Additional or alternative techniques for locking stylet knob 420 on medical device lead 214 may be utilized according to embodiments of the invention.

For example, annular constrictions 422 are provided within interface lumen 417 for use in locking stylet knob 420 onto medical device lead 214 of the illustrated embodiment. Annular constrictions 422 of this example are disposed within interface lumen 417 to correspond with portions of the elongated body of medical device lead 214 disposed between electrical contacts 418. In accordance with some embodiments of the invention, these portions of the elongated body may be composed of an electrically insulative material (e.g., a polymer, such as polyurethane or silicone) which is to some extend compressible. Accordingly, when stylet knob 420 is positioned on proximal end 444 of medical device lead 214, annular constrictions 422 may each compressively engage a corresponding portion of the elongated body of the medical device lead. In accordance with some examples, the relatively rigid configuration of electrical contacts 418 (e.g., electrically conductive surfaces formed from metal) may cooperate with annular constrictions 422 to facilitate locking of stylet knob 420 on medical device lead 214.

Stylet knobs of embodiments of the invention may utilize further additional or alternative techniques for locking the stylet knob onto a medical device lead. For example, a compression latch mechanism may be provided with respect to the stylet knob to controllably reduce the inner diameter of the interface lumen and clamp the stylet knob onto the medical device lead. In accordance with some examples, a locking mechanism may include one or more features disposed upon the medical device lead. For example, a bayonet type connection may be utilized in which one or more small pins are disposed on the proximal end of the medical device lead to engage L-shaped slots on the stylet knob and lock the stylet knob onto the medical device lead.

FIG. 5 shows example operation to anchor a medical device lead using retractable anchor structure of embodiments of the invention. The functions of flow 500 in the example of FIG. 5 may, for example be utilized in anchoring a distal end of a medical device lead when positioning and/or repositioning the medical device lead.

At block 501 of the illustrated embodiment of flow 500, a stylet is inserted into an axial lumen of a medical device lead. For example, stylet 330 may be inserted into axial lumen 317 of medical device lead 214 having retractable tip anchor structure 220 disposed upon distal end 244 of the lead. In accordance with embodiments of the invention, stylet 330 is fully inserted into medical device lead 214 such that a distal end of the stylet engages biasing bulkhead 321 disposed at a terminal end of axial lumen 330 within retractable tip anchor structure 220.

At block 502 of flow 500, bias force is applied to a biasing bulkhead of an anchor structure of the medical device lead via the stylet. For example, a bias force may be applied to a proximal end of stylet 330, whereby that bias force is transferred to biasing bulkhead 321 by a distal end of stylet 330 interfaced with the biasing bulkhead. In accordance with some examples, a stylet knob may be utilized in introducing the bias force to the stylet. For example, stylet knob 420 may be positioned on the proximal end of medical device lead 214 to interface with stylet 330 and subsequently pushed or otherwise moved towards the distal end of medical device lead 214, along a direction of axial lumen 317, to introduce the bias force to stylet 330. Stylet 330 may thus transfer the bias force to biasing bulkhead 321.

In accordance with flow 500 of the illustrated example, a retractable distention of the anchor structure is contracted at block 503. For example, retractable distention 221 may transition to a biased state and be contracted when a suitable bias force is applied to biasing bulkhead 321 of retractable tip anchor structure 220. Sufficient bias force may, for example, be applied via stylet 330 so as to contract retractable distention 321. According to some examples, the bias force may be such that the lead body surface perturbation of retractable distention 321 is contracted to a point that the retractable distention becomes substantially of uniform diameter with the elongated body of medical device lead 214.

At block 504 of the illustrated embodiment of flow 500, the bias force is maintained at the biasing bulkhead. For example, the distal end of stylet 330 may continually engage biasing bulkhead 321 of retractable tip anchor structure 220 to maintain the bias force, thereby holding retractable distention 321 in the biased state and being contracted. According to some examples, stylet knob 420 may be locked onto the proximal end of medical device lead 214 to maintain application of the bias force at biasing bulkhead 321 via stylet 330.

At block 505 of flow 500, the medical device lead may be positioned or repositioned. For example, distal end 244 of medical device lead 214 having retractable distention 221 contracted may be positioned so as to place one or more of electrodes 218 adjacent or in proximity to select tissue (e.g., a select one of the peripheral nerves). In accordance with an example in which the distal end of a medical device lead is positioned, a distal end portion of medical device lead 214 including retractable tip anchor structure 220 may be inserted into the lumen of a needle, the needle inserted into tissue at a desired location, and the distal end portion of the medical device lead implanted in the tissue when the needle is extracted. In an example in which the distal end of a medical device lead is repositioned, the distal end portion of medical device lead 214 including retractable tip anchor structure 220 may be moved axially (e.g., pushed deeper into the tissue or extracted fully or partially from the tissue) through application of appropriate force upon the elongated body of the medical device lead.

At block 506 of flow 500, the bias force is released from the biasing bulkhead. For example, stylet 330 may be partially or fully retracted from axial lumen 317 so that the distal end thereof disengages biasing bulkhead 321 and the bias force released therefrom. According to some examples, stylet knob 420 may be unlocked and partially or fully removed from the proximal end of medical device lead 214 to facilitate backing stylet 330 out of lumen 317.

In accordance with flow 500 of the illustrated example, the retractable distention of the anchor structure is distended to set the anchor within surrounding tissue at block 507. For example, release of the bias force at biasing bulkhead 321 permits retractable distention 321 to transition from the biased state and being contracted to the neutral state and being distended. In accordance with embodiments of the invention, distended retractable distention 321 may engage or otherwise interact with tissue surrounding distal end 244 of medical device lead 214. This interaction between retractable distention 321 and the surrounding tissue discourages movement of distal end 244 of medical device lead 214. In particular, a retractable tip anchor may be deployed, so that the anchor is set within surrounding tissue, by releasing the bias force from the biasing bulkhead (e.g., by unlocking the stylet knob from the proximal end of a medical device lead and backing stylet out retractable tip anchor structure 220).

The retractable tip anchor structure of embodiments of the invention is disposed at or near a distal tip of the medical device lead (e.g., more towards the distal termination point of the lead than are the electrodes), and thus locks the tip of the distal end of the lead into position. The lead tip anchoring resulting from use of a retractable tip anchor configuration provided using the retractable tip anchor structure of embodiments may better prevent and/or reduce movement of a portion of the lead comprising the electrodes as compared to that offered by traditional anchor configurations which are disposed on a portion of the lead near the electrodes more proximal to the IMD. Deployment of a retractable tip anchor of embodiments of the invention provides anchoring of a medical device lead without affecting or moving the placement of the lead electrodes. Moreover, use of retractable tip anchor structure to provide lead tip anchoring according to concepts of the present invention may be used in combination with one or more traditional anchor systems (e.g., lead body anchor, tine anchor, etc.) that are disposed on a portion of the lead near the electrodes more proximal to the IMD. Configurations utilizing both anchoring techniques may offer superior prevention and/or reduction of movement of the electrodes, such for use in situations where movement is likely to be experienced and/or is particularly detrimental.

Although a single iteration of flow 500 has been described above, it should be appreciated that some or all of the functions of flow 500 may be repeated in operation according to some embodiments. For example, operations according to one or more of blocks 501-507 may be repeated so that the retractable tip anchor may be deployed and retracted if repositioning, including explantation, of the medical device lead is desired. In operation according to embodiments of flow 500, a retractable tip anchor may be deployed and intra-operative testing performed (e.g., delivery of stimulation through the electrodes to the tissue, with the patient reporting whether stimulation is felt in the intended location), wherein if relocation of the electrodes is indicated the retractable tip anchor may be retracted, the distal end of the medical device lead repositioned, and the retractable tip anchor again deployed.

Example embodiments have been described above with reference to a single instance of retractable distention in order to simplify the discussion for understanding concepts of the present invention. It should be appreciated, however, that a plurality of retractable distentions may be provided with respect to an anchor structure implemented according to concepts herein. Moreover, anchor structure comprising one or more retractable distentions of the present invention may be disposed on a lead at a location other than shown in the illustrated examples. For example, an anchor structure comprising one or more retractable distentions may be disposed on a portion of the lead near the electrodes more proximal to the IMD according to some embodiments.

Although the present disclosure and its advantages have been described in detail, it should be understood that various changes, substitutions and alterations can be made herein without departing from the spirit and scope of the design as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the present disclosure, processes, machines, manufacture, compositions of matter, means, methods, or steps, presently existing or later to be developed that perform substantially the same function or achieve substantially the same result as the corresponding embodiments described herein may be utilized according to the present disclosure. Accordingly, the appended claims are intended to include within their scope such processes, machines, manufacture, compositions of matter, means, methods, or steps.

Moreover, the scope of the present application is not intended to be limited to the particular embodiments of the process, machine, manufacture, composition of matter, means, methods and steps described in the specification.

What is claimed is:

1. An anchor system for a medical device lead, the anchor system comprising:
   an elongated body portion having an axial lumen;
   retractable distention formed in the elongated body portion, wherein the retractable distention is distended when in a neutral state and is contracted when in a biased state;
   a biasing bulkhead terminating the axial lumen and configured to receive a bias force sufficient to retract the retractable distention; and
   a stylet locking feature disposed in association with an entry of the axial lumen into the elongated body portion, wherein the stylet locking feature is configured for locking a stylet knob onto the medical device lead and maintaining the bias force on the biasing bulkhead with the retractable distention being held as contracted.

2. The anchor system of claim 1, wherein the elongated body portion comprises a portion of an elongated body of the medical device lead and the biasing bulkhead comprises a termination point of the axial lumen at a distal end of the medical device lead.

3. The anchor system of claim 2, wherein the retractable distention is composed of a resilient polymeric material.

4. The anchor system of claim 2, wherein the retractable distention comprises:
   a surface perturbation formed in the elongated body portion, wherein the surface perturbation is distended when the retractable distention is in a neutral state and is contracted when the retractable distention is in a biased state.

5. The anchor system of claim 2, wherein the retractable distention is disposed more near the distal end of the medical device lead than are electrodes disposed along the distal end of the medical device lead.

6. The anchor system of claim 5, wherein electrical contacts of the medical device lead are disposed along a proximal end of the medical device lead, and wherein each electrical contact of the electrical contacts disposed along the proximal end of the medical device lead is in electrical communication with a respective electrode of the electrodes disposed along the distal end of the medical device lead.

7. The anchor system of claim 1, wherein the biasing bulkhead is configured to receive the bias force applied in an axial direction corresponding to the axial lumen, wherein the retractable distention transitions to the biased state and being contracted when the bias force is present on the biasing bulkhead and the retractable distention transitions to the neutral state and being distended when the bias force is removed from the biasing bulkhead.

8. The anchor system of claim 7, further comprising:
a stylet configured to interface with the biasing bulkhead at a first end of the stylet and apply the bias force to the biasing bulkhead when a portion of the stylet is passed through the axial lumen; and
the stylet knob configured to interface with a second end of the stylet and provide the bias force to be transferred via the stylet to the biasing bulkhead.

9. The anchor system of claim 8, wherein the stylet knob is configured to lock on to the stylet locking feature on a proximal end of the medical device lead and maintain the bias force.

10. The anchor system of claim 1, further comprising:
a plurality of retractable distentions formed in the elongated body portion, wherein the plurality of retractable distentions includes the retractable distention, wherein each retractable distention of the plurality of retractable distentions is distended when in a neutral state and is contracted when in a biased state, wherein the biasing bulkhead is configured to receive the bias force applied in an axial direction corresponding to the axial lumen, and wherein each retractable distention of the plurality of retractable distentions transitions to the biased state and being contracted when the bias force is present on the biasing bulkhead and transitions to the neutral state and being distended when the bias force is removed from the biasing bulkhead.

11. A method comprising:
contracting a retractable distention of an anchor structure by applying a bias force to a biasing bulkhead of the anchor structure, wherein the retractable distention is formed in an elongated body having an axial lumen, and wherein the biasing bulkhead is disposed at a termination point of the axial lumen;
distending the retractable distention of the anchor structure by relieving the bias force from the biasing bulkhead of the anchor structure
inserting a stylet into the axial lumen prior to contracting the retractable distention; and
locking a stylet knob onto an end of a medical device lead comprising the elongated body after contracting the retractable distention of the anchor structure, wherein locking the stylet knob onto the end of the medical device lead results in the stylet maintaining the bias force on the biasing bulkhead and the retractable distention being held as contracted.

12. The method of claim 11, wherein the retractable distention is distended when in a neutral state and is contracted when in a biased state, and wherein the retractable distention transitions to the biased state and being contracted when the bias force is present on the biasing bulkhead and transitions to the neutral state and being distended when the bias force is removed from the biasing bulkhead.

13. The method of claim 11, wherein the anchor structure comprises a retractable tip anchor disposed on a distal end of a medical device lead between a closed end of the axial lumen and all electrodes of the medical device lead.

14. The method of claim 11, wherein the bias force is applied in an axial direction corresponding to the axial lumen.

15. The method of claim 11, further comprising:
positioning a distal end of the medical device lead including the elongated body in which the retractable distention is formed prior to the distending the retractable distention; and
unlocking the stylet knob from the medical device lead after the positioning the distal end, wherein the unlocking the stylet knob from the end of the medical device lead results in the stylet releasing the bias force on the biasing bulkhead and the retractable distention allowed to distend.

16. The method of claim 15, further comprising:
re-locking the stylet knob onto the medical device lead after the distending the retractable distention of the anchor structure, wherein the re-locking the stylet knob onto the end of the medical device lead results in the stylet again maintaining the bias force on the biasing bulkhead and the retractable distention being held as contracted;
re-positioning the distal end of the medical device lead including the elongated body in which the retractable distention is formed;
re-unlocking the stylet knob from the medical device lead after the re-positioning the distal end, wherein the re-unlocking the stylet knob from the end of the medical device lead results in the stylet releasing the bias force on the biasing bulkhead; and
re-distending the retractable distention of the anchor structure by the releasing the bias force from the biasing bulkhead of the anchor structure.

17. The method of claim 11, wherein the stylet knob includes a stylet locking feature having one or more annular constrictions disposed within an interface lumen of the stylet knob, and wherein locking the stylet knob onto the end of the medical device lead comprises:
engaging the one or more annular constrictions with one or more portions of the elongated body disposed to correspond with the one or more annular constrictions.

18. The method of claim 11, wherein the elongated body includes one or more electrical contacts disposed along a proximal end of the medical device lead to cooperate with one or more annular constrictions within an interface lumen of the stylet knob facilitating locking of the stylet knob on the medical device lead.

19. The anchor system of claim 1, wherein the stylet locking feature comprises:
one or more portions of the elongated body portion disposed to correspond with one or more annular constrictions within an interface lumen of the stylet knob and configured to compressively engage the one or more annular constrictions.

20. The anchor system of claim 1, wherein the stylet locking feature comprises:
one or more electrical contacts disposed to cooperate with one or more annular constrictions within an interface lumen of the stylet knob to facilitate locking of the stylet knob on the medical device lead.

21. The anchor system of claim 1, wherein the stylet locking feature comprises:

a locking mechanism disposed upon the medical device lead.

\* \* \* \* \*